US006218149B1

(12) United States Patent
Morrison et al.

(10) Patent No.: US 6,218,149 B1
(45) Date of Patent: Apr. 17, 2001

(54) ANTIBODIES HAVING MODIFIED CARBOHYDRATE CONTENT AND METHODS OF PREPARATION AND USE

(75) Inventors: Sherie L. Morrison, Los Angeles; Vernon T. Oi; Paul R. Hinton, both of Mountain View, all of CA (US)

(73) Assignee: The Trustees of Columbus University in the City of New York, New York, NY (US)

( * ) Notice: Subject to any disclaimer, the term of this patent is extended or adjusted under 35 U.S.C. 154(b) by 0 days.

(21) Appl. No.: 08/458,666

(22) Filed: Jun. 2, 1995

Related U.S. Application Data

(63) Continuation of application No. 08/251,529, filed on May 19, 1994, now abandoned, which is a continuation of application No. 07/938,557, filed on Aug. 28, 1992, now abandoned, which is a continuation of application No. 07/244,744, filed on Sep. 15, 1988, now abandoned.

(51) Int. Cl.$^7$ .................................................. A61K 39/395
(52) U.S. Cl. .................. 435/69.6; 435/455; 435/328; 530/387.3; 530/395; 514/8; 536/23.53; 536/133.1
(58) Field of Search .............. 536/23.53; 435/69.6, 435/70.21, 172.2, 320.1, 240.27, 328, 455; 935/15; 424/133.1; 530/387.3, 395

(56) References Cited

FOREIGN PATENT DOCUMENTS 8807089   9/1988   (WO).

OTHER PUBLICATIONS

Alberts et al, *Molec. Biol. of Cell*, 3$^{rd}$Edition, Garland Publ., 136 Madison Ave, Ny, Ny, 10016, pp 344–349 and 375, 1983.*

Tachibana et al Biochem Biphys Res Commun 189(2) 625, 1992.*

Endo et al Molec Immunology 32(13):931, 1995.*

Wright et al EMBO J vol. 10(1) 2717, 1991.*

Wright et al Springer Seminars in Immunology 15(2–3) 259, 1993.*

Knight et al BioTechnology vol. 17 No. 1, Jan. 1989.*

*Molecular Biology Of The Cell*, Alberts et al. ed. Garland Publishing , Inc., 136 Madison Ave, NY , NY, 10016, pp. 344–349 (1983).

Labeta et al. Immunology 57: 311–317 (1986). Structure of Asymmetric Non–Preciptating Antibody .*

Zoller et al., Methods of Enzymology 154:329 (1987). Olignucleotide–Directed Mutagenesis.*

Matsuuchi et al J of Immunology 125:5 2188–2190, 1981.*

Wigzell et al 1983, Proceedings of Natl. Acad. Sci. 80: 6632–6636.*

Kabat et al 1987 J of Immunology 138:12 4472–4479.*

Morrison and Kabat 1988 J of Experimental Medicine 168: 1099–1109.*

J. Sharon et al. (1986) PNAS 83:2628–2631.

J. Sharon et al. (Apr. 1988) J. Immunol. 140(8):2666–2669.

Weiss et al. (1985) Eur. J. Immunol. 15:768–772.

Akolkar et al. (1987) The Journ of Immunol. 138(12):4472–4479.

Wilke et al. (1987) Chemical Abstracts 107(7), abst. No. 57077n.

Morrison et al (1984) Chimeric human antibody molecules: mouse antigen–binding domains with human constant region domanis, Proc Nat'l Acad Sci USA 81, 6851–6855.

Verhoeyen et al (Mar. 25, 1988) Reshaping human antibodies: grafting an antilysozme activity, Science 239, 1534–1536.

Reichmann et al (Mar. 24, 1988) Reshaping human antibodies for therapy, Nature 332, 323–327.

Abel et al (1986) The carbohydrate content of fragments and polypeptide chains of human γG–myeloma proteins of different heavy–chain subclasses, Biochemistry 7, 1271–1278.

Sox and Hood (1970) Attachment of carbohydrate to the variable region of myeloma immunoglobulin light chains, Proc Nat'l Aca Sci USA 66, 975–979; and.

Spiegelberg et al (1970) Localization of the carbohydrate within the variable region of light and heavy chains of human γG myeloma proteins.

Biochemistry 9, 4217–4223.

* cited by examiner

*Primary Examiner*—Julie Reeves
(74) *Attorney, Agent, or Firm*—John P. White; Cooper & Dunham LLP

(57) ABSTRACT

This invention provides a method of altering the affinity of an antibody for the antigen to which it is directed which comprises introducing into the variable region of the antibody a carbohydrate recognition site under conditions such that a carbohydrate binds to the site and thus attaches to the antibody. This invention also provides a method of modifying the carbohydrate content of an antibody which comprises deleting from a constant region of the antibody a carbohydrate recognition site which naturally occurs in such constant region of such antibody. Antibodies, e.g., monoclonal antibodies and human monoclonal antibodies, diagnostic test kits, DNA encoding antibodies, therapeutic agents, and methods for detecting the presence of a substance in a sample, and for recovering and purifying a substance from a sample are also provided.

**

FIGURE 3A
1 2 3 4 5 6

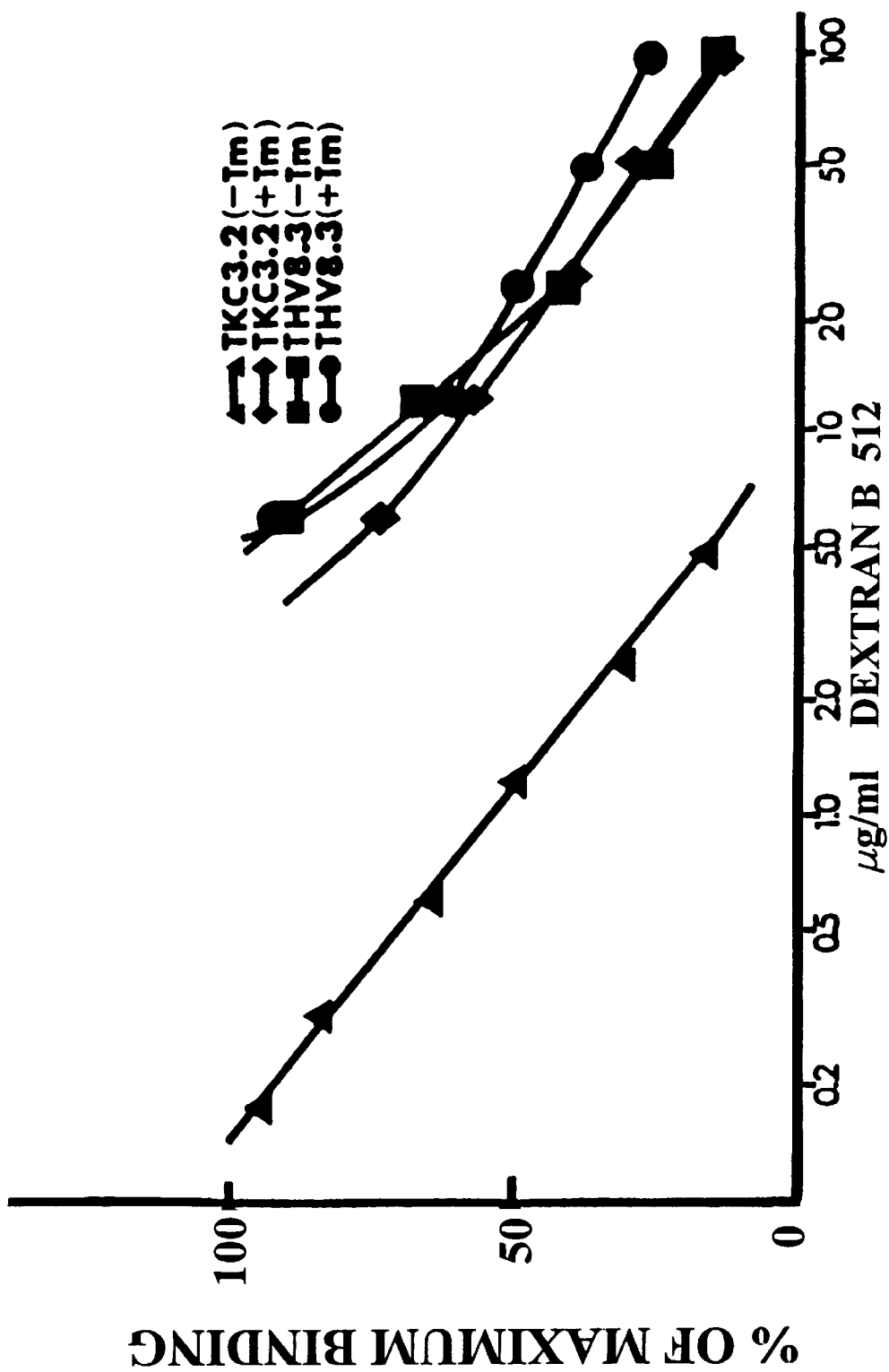

ANTIBODIES HAVING MODIFIED CARBOHYDRATE CONTENT AND METHODS OF PREPARATION AND USE

This is continuation of U.S. Ser. No. 08/251,529, filed May 31, 1994, now abandoned, a continuation of U.S. Ser. No. 07/938,557, filed Aug. 28, 1992, now abandoned, continuation of U.S. Ser. No. 07/244,744, filed Sep. 15, 1988 now abandoned, the contents of which are hereby incorporated by reference.

The invention described herein was made, in part, in the course of work under Grant Numbers AI 19042, CA 16858, CA 22736 and CA 13696 from the National Institute for Health, U.S. Department of Health and Human Services. The U.S. Government has certain rights in this invention.

BACKGROUND OF THE INVENTION

Throughout this application, various publications are referenced by Arabic numerals. Full citations for these references may be found at the end of the specification immediately preceding the claims. The disclosures of these publications in their entireties are hereby incorporated by reference into this application to describe more fully the state of the art to which this invention pertains.

Immunochemical characterization of antibodies to alpha (1→6) dextran has given insights into the size and shape of the antibody combining site and the nature of the interaction between antibodies and antigen. In this regard, it would be useful to correlate the immunochemical properties of the anti-dextran antibodies with their primary structure. In the course of these studies, cDNAs from three monoclonal anti-alpha (1→6) dextran hybridoma cell lines, 14.6b.1, 5.54.4.24.1, and 19.22.1, were cloned (1) and the nucleotide sequences of the variable regions of the heavy chain ($V_H$) and of the light chain ($V_L$) determined (2) (see Table I on page 22 of this application). All synthesize an identical kappa light chain with the $V_{kappa}$-OX1 germline gene (3) rearranged to the $J_{kappa}2$ segment and the heavy chains differ by only one or two amino acids in their complementarity-determining regions (CDRs). When compared to 14.6b.1, 5.54.4.24.1 and 19.22.1 have an identical Thr→Asn amino acid change at position 60 in the variable region of the heavy chain ($V_H$); 5.54.4.24.1 has an additional change (Ser→Gly) at position 31 in complementarity-determining region 1 (CDR1). The changes in heavy chain sequence result in 5.54.4.24.1 and 19.22.1 having a (ten) 10 fold or greater reduction in their binding constant for both polymeric dextran and isomaltoheptaose (IM7) when compared to 14.6b.1 (Table I).

The Thr→Asn change in 5.54.4.24 and 19.22.1 leads to the loss of a potential N-linked glycosylation site (Asn 58-Tyr 59-Thr 60) present in 14.6b.1. One of the purposes of this study and the present invention was to determine whether this potential N-linked glycosylation site is glycosylated, and if so, whether the addition of carbohydrate to complementarity-determining region 2 (CDR2) affects the binding constant for dextran. It is difficult to demonstrate glycosylation of $V_H$ directly since both Immunoglobulin A (IgA) and Immunoglobulin M (IgM) isotypes are glycosylated within their $C_H1$ domains and carbohydrate present in Fd could be linked to either $V_H$ or constant region of the heavy chain ($C_H$). Fd is the product resulting from the chemical or enzymatic cleavage of the antibody and comprises the heavy chain of the variable region and the heavy chain of the constant region of the antibody. Therefore, the three $V_H$ regions have been transferred to the human $IgG_4$ constant region which is devoid of carbohydrate in its $C_H1$ domain. In this invention, the presence of carbohydrate is demonstrated to be within the $V_H$ of 14.6b.1. Comparison of the association constants for aglycosylated, tunicamycin treated and untreated antibodies shows that the presence of carbohydrate increases the apparent association constant (aKa) of 14.6b.1 for dextran. The effect on binding is unique to the carbohydrate present in $V_H$ since absence of carbohydrate from $C_H2$ does not change the aKa for dextran.

By introducing into an antibody a carbohydrate recognition site for the attachment of carbohydrate, purification of the antibody can be enhanced because the carbohydrate is attached to the outside of the antibody and thus, is more accessible to binding by lectin (purification).

In this invention, the carbohydrate content of an antibody may be modified by adding or deleting carbohydrate recognition sites in the constant region of the antibody. In so doing, effector functions of the antibody are modified. Carbohydrate recognition sites in the constant region can also serve as sites for labelling, e.g., radionuclides, such as $^{125}I$.

SUMMARY OF THE INVENTION

This invention concerns a method of altering the affinity of an antibody for the antigen to which it is directed which comprises introducing into the variable region of the antibody a carbohydrate recognition site under conditions such that a carbohydrate binds to the site and thus attaches to the antibody.

This invention also concerns a method of producing an antibody which may be more readily recovered or purified which comprises introducing into the variable region of the antibody a carbohydrate recognition site under conditions such that a carbohydrate binds to the site and thus attaches to the antibody.

This invention further provides an antibody which does not occur in nature and which comprises a carbohydrate recognition site genetically engineered into a variable region of the antibody which does not naturally include a carbohydrate recognition site in such variable region.

Still further, the present invention provides a method of modifying the carbohydrate content of an antibody which comprises deleting from a constant region of the antibody a carbohydrate recognition site which naturally occurs in such constant region of such antibody.

The invention also provides a method of modifying the carbohydrate content of an antibody which comprises adding to a constant region of the antibody a carbohydrate recognition site which does not naturally occur in such constant region of such antibody.

This invention further concerns a human antibody which does not occur in nature and which is characterized by the absence of a carbohydrate recognition site in a constant region of the antibody which naturally includes such a carbohydrate recognition site in such constant region.

Further, this invention provides a human antibody which does not occur in nature and which is characterized by the presence of a carbohydrate recognition site in a constant region of the antibody which does not naturally include such a carbohydrate recognition site in such constant region.

Finally, this invention provides therapeutic agents derived from, and DNA encoding, the antibodies, of the invention as well as sensitive methods for detecting the presence of substances in a sample, methods for recovering a substance from a sample containing the substance and for purifying such substance, and diagnostic test kits.

BRIEF DESCRIPTION OF THE FIGURES

In FIG. 2A the TKC3.2 (Fab) and TKC3.2 samples were analyzed on a separate SDS-PAGE gel.

FIG. 3A and 3B. 12.5% Tris-glycine SDS-PAGE analysis of [$^{35}$S]-Met labelled transfectoma culture supernatants, immunoprecipitated with rabbit anti-human Ig fragment constant region (Fc) antiserum following Concanavalin A (Con A) adsorption (as indicated) and/or tunicamycin treatment. Tunicamycin at a concentration of 8 micrograms/ml (Boehringer Mannheim, West Germany) was used to inhibit N-Linked glycosylation. Cells were biosynthetically labelled for three hours with [$^{35}$S]-Met in the presence of tunicamycin, the secreted Ig in the culture supernatant discarded, the cells washed with Ipco Modified Dulbecco's Medium (IMDM) medium twice; fresh tunicamycin and [$^{35}$S]-Met was added; and treatment continued overnight at 37° C. Samples were reduced with 0.15 M beta-mercaptoethanol prior to SDS-PAGE. The positions of the H and L chains are indicated.

3A. Con A-sepharose adsorption of secreted transfectoma Ig. Lanes 1 and 6, untreated TKC3.2 ($V_H$ 14.6b.1) and THV8.3 ($V_H$ 19.22.1) secreted immunoglobulin, respectively. Lanes 2 and 4, TKC3.2 unbound, and TK3.2 bound and eluted from Con A. Sepharose, lanes 3 and 5, THV8.2 unbound, and bound and eluted from Con A Sepharose.

3B. Tunicamycin treated cell supernatants without or with Con A-Sepharose adsorption. Lanes 1 and 2, TKC3.2 ($V_H$ 14.6b.1) before and after tunicamycin treatment; lanes 3 and 4, THV8.3 ($V_H$ 19.22.1) before and after tunicamycin treatment; lanes 5 and 6, tunicamycin treated TKC3.2 Con A supernatant and eluate, respectively; lanes 7 and 8, tunicamycin treated THV8.3 Con A supernatant and eluate, respectively.

FIG. 4. Inhibition by soluble dextran of antibody binding to dextran coated ELISA plates. Percentage of antibody binding (ordinate) is plotted against dextran inhibitor concentration (abscissa). Plates were coated with 20 micrograms/ml dextran. Native antibodies and antibodies aglycosylated by tunicamycin treatment were used; trace quantities of glycosylated Ig present in tunicamycin treated TKC3.2 was removed by adsorption to Con A Sepharose.

Apparent binding constants were determined using the method of Nieto et. al. (25). In brief, the association constant for an antibody is defined as the reciprocal free ligand concentration necessary for occupancy of one-half of the antibody binding sites. If a fixed amount of antibody Ab is reacted with increasing amounts of free ligand on a plate coated with solid-phase antigen, the reciprocal of the free ligand concentration which causes 50% inhibition of binding to the plate is a function of the intrinsic Ka, i.e., the apparent affinity constant (aKa). Calculation for the constant is carried out by interpolation of the inhibition curve assuming linearity near the point of 50% binding. The following experimental conditions have been employed to measure the aKa values. Corning microtiter plates were coated with 0.5 micrograms/ml or 20 micrograms/ml dextran B512 (high affinity and low affinity assay conditions, respectively). Bound immunoglobulin Ig was quantitated using anti-human IgG labelled with horseradish peroxidase.

Figure 5:
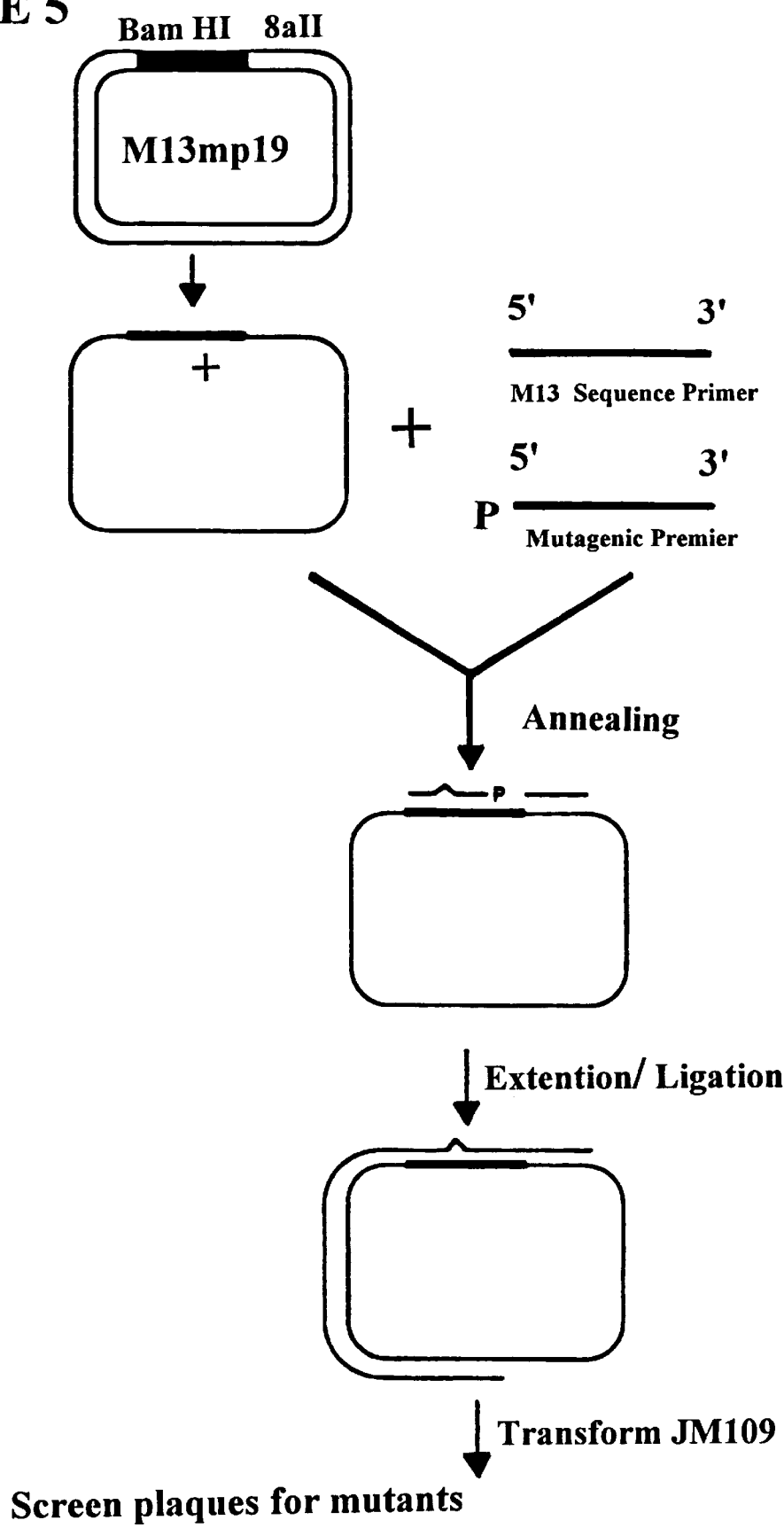

FIG. 5. General scheme for two primer site-directed mutagenesis. The Sal I-Bam HI fragment containing the IgG constant region exon is cloned into the M13 phage M13mp19 at the polylinker site. The positive-strand DNA template of the recombinant phage is prepared by the standard polyethylene glycol method. Two primers are used to produce the mutation, one the M13 sequencing primer, the other a 5' end-phosphorylated mutagenic primer with one nucleotide mismatched in the consensus glycosylation sequence. Both primers are annealed to the template at the same time. After primer extension and ligation, the mutant/wild-type-gapped heteroduplex is used to transform *E. coli* host JM109.

DETAILED DESCRIPTION OF THE INVENTION

The present invention concerns a method of altering the affinity of an antibody for the antigen to which it is directed which comprises introducing into the variable region of the antibody a carbohydrate recognition site or sites under conditions such that a carbohydrate binds to the site and thus attaches to the antibody.

As used in the context of this invention, the term "antibody" includes all types of antibodies including both human, non-human antibodies, and chimeric antibodies, both monoclonal and polyclonal antibodies, and all antibody isotypes, including the major classes of humoral immunoglobulins in humans, IgG, IgM, IgA, IgD, and IgE. In one embodiment of this invention, the antibody is a monoclonal antibody; in another, the antibody is a human antibody.

The affinity of an antibody for the antigen to which it is directed may be measured using techniques well known in the art. The affinity or binding of an antibody may be measured, for purpose of illustration, as follows. The association constant for an antibody is defined as the reciprocal free ligand concentration necessary for occupancy of one-half of the antibody binding sites. If a fixed amount of antibody is reacted with increasing amounts of free ligand on a plate coated with solid-phase antigen, the reciprocal of the free ligand concentration which causes 50% inhibition of binding to the plate is a function of the intrinsic Ka, i.e., the apparent affinity constant (aKa). Calculation of the constant may be carried out by interpolation of the inhibition curve assuming linearity near the point of 50% binding.

As used herein, the carbohydrate recognition site includes any specific amino acid sequence in an antibody to which a carbohydrate will specifically attach to the antibody. The presently best known such carbohydrate recognition site that is useful in accordance with teachings of the present invention, is the amino acid sequence:

Asn-X-Thr/Ser wherein X may be any amino acid and Thr/Ser indicates a threonine or a serine. Such a site or sites may be introduced into the variable region of the antibody using methods well known in the art to which this invention pertains. See, for example, "In Vitro Mutagenesis," *Recombinant DNA: A Short Course,* J. D. Watson, et al. W.H. Freeman and Company, New York, 1983, chapter 8, pp. 106–116. A particularly useful form of in vitro mutagenesis, also well-known to those skilled in the art, is site-directed mutagenesis, which is described in *Recombinant DNA: A Short Course* and is exemplified in the Experimental Details section which follows.

Thus, the carbohydrate recognition site may be introduced into the antibody by modifying or mutating an amino acid sequence so that the desired Asn-X-Thr/Ser sequence is obtained. If the sequence has an asparagine, or a threonine or serine, then at the next position two amino acids removed, a corresponding threonine or serine; or an asparagine, may be introduced, respectively, in order to obtain the desired Asn-X-Thr/Ser sequence, so that the antibody will then bind carbohydrate to the antibody.

Although the carbohydrate recognition site may be introduced anywhere in the variable region of the antibody, this is provided only that its introduction does not destroy the ability of the antibody to bind antigen. Presently, it is preferred that the carbohydrate recognition site be introduced into that portion of the variable region known as the second hypervariable region or complementarity-determining region (CDR2). Thus, this invention provides a method of altering the affinity of an antibody for the antigen to which it is directed by introducing a carbohydrate recognition site into the second hypervariable region of the antibody. In another embodiment this invention provides a method for altering the affinity of an antibody. In this method, a carbohydrate recognition site is introduced into a variable region of an antibody which does not normally include a carbohydrate recognition site. Numerous methods exist for introducing the carbohydrate recognition site into the antibody and are well known to those skilled in the art to which this invention relates. For example, the carbohydrate recognition site may be introduced into the variable region of the antibody by site-directed mutagenesis of DNA encoding the variable region of the antibody.

This invention also provides a method of producing an antibody which may be more readily recovered or purified which comprises introducing into the variable region of the antibody a carbohydrate recognition site under conditions such that a carbohydrate binds to the site and thus attaches to the antibody, for example, a mouse or human monoclonal or polyclonal antibody. Once again the carbohydrate recognition site is preferably introduced into a variable region of the antibody which does not normally include a carbohydrate recognition site, particularly the second hypervariable region of the antibody, using methods well known to those skilled in the art as are conditions for doing so under which carbohydrate attaches to the resulting antibody. In this embodiment of the invention it is also presently preferred that the carbohydrate recognition site be introduced into the variable region of the antibody by site directed mutagenesis of DNA encoding the variable region of the antibody.

Those skilled in the art will readily appreciate that one of the limitations associated with the use of antibodies, particularly monoclonal antibodies, is the ability to recover the antibodies in high yield and at high levels of purity without denaturing the antibody. The ability to introduce a carbohydrate onto the exposed variable region of an antibody will greatly facilitate such recovery, for example, by permitting the use of adsorption chromatography onto a lectin.

This invention concerns an antibody, e.g., a mouse or human monoclonal or a human polyclonal antibody, which does not occur in nature and which comprises a carbohydrate recognition site genetically engineered into a variable region of the antibody which does not naturally include a carbohydrate recognition site in such variable region. In one embodiment, the antibody is characterized by enhanced affinity for the antigen to which it is directed. The antibody may additionally comprise a carbohydrate attached to the carbohydrate recognition site which has been introduced or genetically engineered into the variable region of the antibody, e.g., into the second hypervariable region of the antibody.

This invention also concerns an antibody in accordance with this invention labelled with a detectable marker. For example, the antibody may have a detectable marker attached to, or incorporated into, one or more of the amino acids or carbohydrate which comprise its structure. Such a marker may be any molecule or reagent which is capable of being detected, such as a chromophore, a fluorophore or a radioactive moiety, e.g., $^{125}I$. Additionally, the detectable marker may be an enzyme which catalyzes a reaction producing a detectable product, a chemiluminescent catalyst, biotin or a metal ion detectable by nuclear magnetic resonance. Other suitable detectable markers include ligands capable of binding to specific proteins which have been tagged with an enzyme, e.g., horseradish peroxidase. One example of a suitable ligand is biotin, which will bind to avidin or streptavidin. Another suitable ligand is a hemin molecule, which will bind to the apoenzyme portion of catalase. Those skilled in the art will be readily familiar with methods for attaching or introducing such detectable markers onto antibodies and for using antibodies which are so labelled.

In still another embodiment, this invention provides a solid support to which an antibody according to the invention is bound. The solid support may be in the form of a column for chromatographic separations or may be a bed or plate or the like for diagnostic application. The solid support may comprise, for example, silicaceous, cellulosic, plastic material, controlled pore glass, sepharose, cyanogen bromide- or DBM activated-paper, or nitrocellulose.

In another aspect, this invention provides an altered antibody prepared by the method described herein in which the affinity of the antibody for the antigen to which it is directed is altered by introducing into the variable region of the antibody a carbohydrate recognition site or sites under conditions such that a carbohydrate binds to the site and thus attaches to the antibody. The present invention further contemplates deoxyribonucleic acid, DNA, encoding such an antibody. Methods to determine and produce DNA that encode specific antibodies, i.e., specific amino acid sequences, are well known in the art.

This invention still further provides a method of modifying the carbohydrate content of an antibody, e.g., a mouse or human monoclonal or human polyclonal antibody, which comprises deleting from a constant region of the antibody a carbohydrate recognition site or sites which naturally occur in such constant region of such antibody. As described hereinabove, a carbohydrate recognition site useful in accordance with this invention has the amino acid sequence Asn-X-Thr/Ser wherein X may be any amino acid and Thr/Ser indicates a threonine or serine.

Deletion of such a site may be effected, by methods well known to those skilled in the art, for example, by site-directed mutagenesis of DNA encoding such constant region of the antibody, in which an asparagine, or a threonine or serine is replaced by another amino acid leading to deletion of the carbohydrate recognition site and thus preventing attachment of carbohydrate to the antibody.

This invention provides a method of modifying the carbohydrate content of an antibody which comprises adding to a constant region of the antibody a carbohydrate recognition site or sites which does not naturally occur in such constant region of such antibody. This invention also provides a modified antibody so prepared. Once again, addition of the carbohydrate recognition site to the antibody may be effected by site-directed mutagenesis of DNA encoding such constant region of the antibody.

The present invention additionally provides a method of modifying the biological effector function of an antibody which comprises modifying the carbohydrate content of the antibody using the method described hereinabove in which the carbohydrate content of the antibody is modified by deleting from a constant region of the antibody a carbohydrate recognition site or sites which naturally occur in such constant region of such antibody. Biological effector functions of antibodies which may be so modified include such functions as the ability to bind $F_C$ receptor and the ability to activate complement.

Where, according to this invention, a carbohydrate recognition site is to be introduced into, or deleted from a specific region of the antibody, e.g., variable or constant region, the altered or genetically engineered DNA is used to construct a complete antibody gene. In turn, the gene, i.e., DNA sequence, is introduced into an expression vector and subsequently expressed in an appropriate cellular environment. For antibody molecules containing carbohydrate, a eukaryotic cell is preferred. For antibody molecules lacking carbohydrate, a eu- or prokaryotic cell may be used. Those skilled in the art to which this invention relates will readily appreciate the well known techniques, by which such DNA sequences or genes are constructed, the manner of introduction into expression vectors, the types of vectors which are useful, and conditions and manner of expression in an appropriate cellular environment.

This invention also concerns a human antibody, e.g., a human monoclonal antibody, which does not occur in nature and which is characterized by the absence of a carbohydrate recognition site in a constant region of the antibody which naturally includes such carbohydrate recognition site is such constant region. The invention further provides DNA encoding such antibody.

This invention also concerns a human antibody, e.g., a human monoclonal antibody, which does not occur in nature and which is characterized by the presence of a carbohydrate recognition site in a constant region of the antibody which does not naturally include such carbohydrate recognition site in such constant region. The invention further provides DNA encoding such antibody.

The human antibody, e.g., human monoclonal antibody, may have a carbohydrate attached to such carbohydrate recognition site and in one embodiment of this invention, may be employed as a therapeutic agent when a therapeutic ligand such as an anticancer drug such as ricin A chain, radionuclides, e.g., $^{125}I$, or other therapeutant is bound to such carbohydrate attached to such antibody. Such therapeutic agents may be used for example to treat immune system abnormalities or other disease states. Still in other embodiments, this human antibody is labelled, i.e., a label such as a detectable marker is bound to such carbohydrate attached to the antibody.

This invention contemplates a modified antibody prepared by the method described herein in which the carbohydrate content of an antibody is modified by deleting from a constant region of the antibody a carbohydrate recognition site which naturally occurs in such constant region of such antibody as well as DNA encoding such an antibody.

This invention also provides a more sensitive method for detecting the presence of a substance or analyte in a sample, such a human biological fluid sample, which comprises contacting the sample with an antibody directed to the substance. The antibody may be labelled with a detectable marker, e.g., a chromophore, a fluorophore or a radioactive moiety. Such an antibody as described hereinabove is one which does not occur in nature and which comprises a carbohydrate recognition site genetically engineered into a variable region of the antibody which does not naturally include a carbohydrate recognition site in such variable region. In this method the contacting is performed under conditions such that any substance or analyte present in the sample forms a detectable complex with the antibody and then detecting the presence of such complex and thus the presence of the substance. In one embodiment the antibody so employed is bound to a solid support of the type described hereinabove.

The amount or concentration of the substance or analyte in the sample may also be qualified by determining the amount of complex formed, and thereby the amount or concentration of the substance or analyte, for example by comparison with a known amount of the substance or analyte. The quantitative determination of the amount or of complex formed by the substance and of the antibody directed to substance in a sample may be accomplished using methods which depend upon the identity of the detectable moiety but which are nevertheless in the well known art. Thus, if the detectable moiety is radioactive, a liquid scintillation counter may be employed. If the moiety is an enzyme, such as horseradish peroxidase in a standard assay, a spectrophotomer may be employed. If the moiety is flourescent, a fluorometer may be used. One particularly useful approach involves fluorescence activated cell sorting by means of which the method may be conveniently, rapidly and accurately carried out.

This invention still further provides a method of recovering a substance from a sample containing the substance which comprises contacting the sample with antibody directed to the substance. The antibody has been described hereinabove as one which does not occur in nature and which comprises a carbohydrate recognition site genetically engineered into a variable region of the antibody which does not naturally include a carbohydrate recognition site in such variable region. Contacting is effected appropriate conditions such that substance in the sample forms a complex with the antibody. The substance is then recovered from the resulting complex. In a further aspect, such a method is a chromatographic one in which the antibody is bound to a solid support packed into a column.

This invention also contemplates a purification method for a substance which comprises recovering the substance from a sample containing the substance using the method, just described above, from a sample under conditions such that the substance is recovered in purified form.

This invention yet further concerns a diagnostic kit comprising the antibody, described above, which does not occur in nature and which comprises a carbohydrate recognition site genetically engineered into a variable region of the antibody which does not naturally include a carbohydrate recognition site in such variable region. Additionally, this invention provides a diagnostic kit comprising such an antibody labelled with a detectable marker, such as a chromophore, fluorophore or radioacive moiety. The various method for detecting the presence of a substance in a sample and for recovering a substance from a sample containing the substance are based upon the novel antibodies of this invention and the substances forming a complex, and are described more fully herein.

The types of assays that are useful in the methods provided by the present invention are well known to those skilled in the art pertaining to this invention. Among such assays are liquid-phase assays, such as radioimmunoassays, and solid-phase assays, such as ELISA (Enzyme Linked Immunosorbent Assays) and the sandwich or IRMA (Immuno Radio-Metric Assay) assay. With respect to the latter assay, a particularly useful immunometric assay is the "two-site" or "sandwich" immunometric assay technique disclosed by David, et al., U.S. Pat. No. 4,376,110, the contents of which are hereby incorporated by reference. Assay conditions such as time of assay, pH, temperature, ionic strength of the assay, are also known to those skilled in the art. A general description of such widely known assays and conditions are described in *Laboratory Techniques in Biochemistry and Molecular Biology*, vol. 13, *Monoclonal Antibody Technology*, A. M. Campbell, Elsevier, N.Y., 1986, chapter 2, "Assay Techniques," pp. 33–65.

This invention is illustrated in the Experimental Detail Discussion section which follow. These sections are set forth to aid in an understanding of the invention but are not intended to, and should not be construed to, limit in any way the invention as set forth in the claims which follow thereafter.

EXPERIMENTAL DETAILS

First Series of Experiments

Materials and Methods

Figure 1:
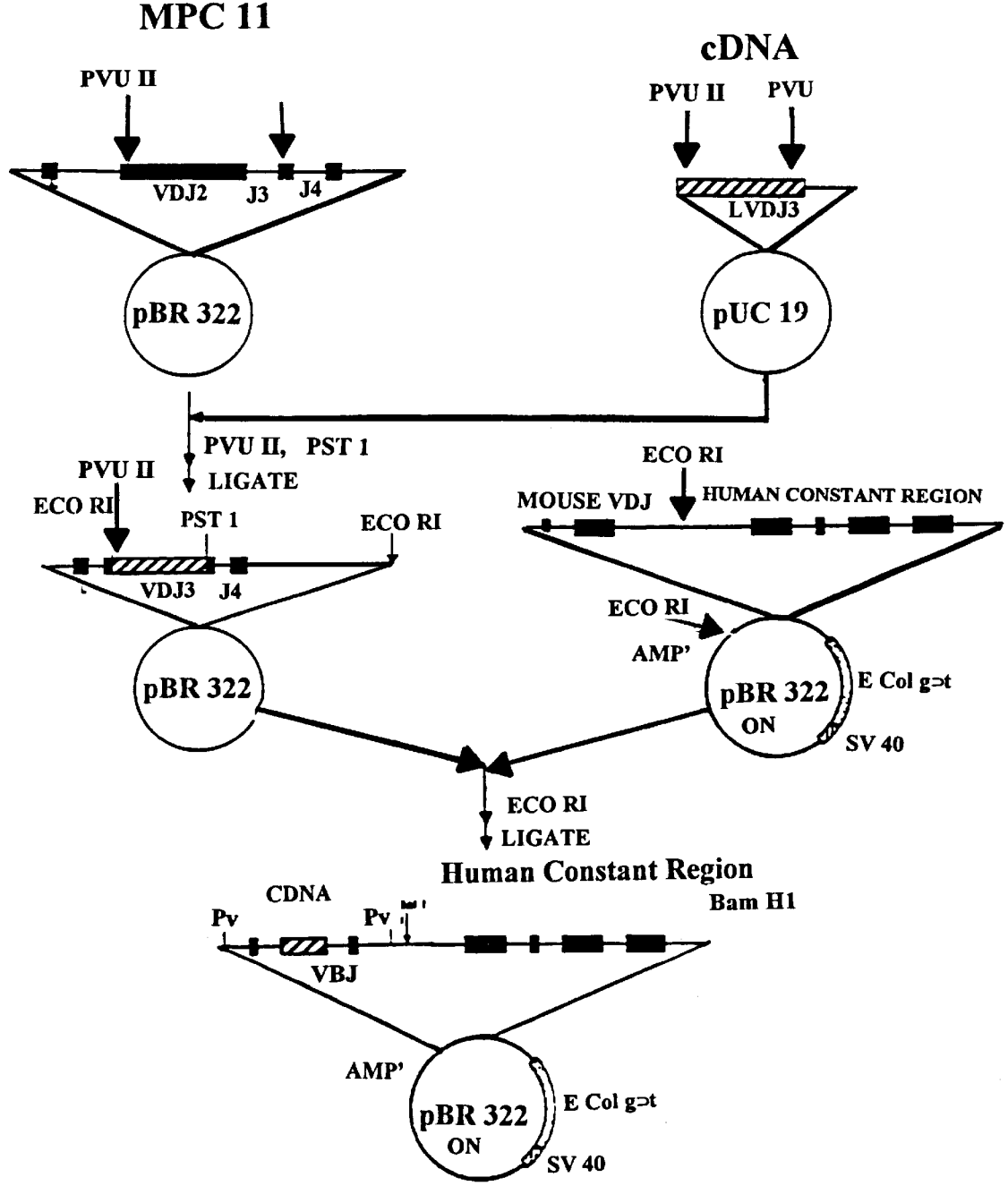
FIG. 1. Substitution of the genomic $V_H$ region with $V_H$ cDNA and isotype switch. A genomic EcoRI fragment containing the MPC11 H chain promoter, leader sequence, rearranged V region, and Ig enhancer (22) was cloned into the EcoRI site of a pBR322 derivative deleted of nucleotide 2065 through 29. Using cDNA produced from the anti-alpha (1→6) dextran hybridomas (2), the V region of MPC11 was replaced by the anti-dextran V region by inserting the PvuII-PstI cDNA fragment into PvuII-PstI cleaved MPC11. The first four $V_H$ amino acids are derived from MPC11, but are identical to those found in the three cDNAs (22). The EcoRI fragment containing the dextran $V_H$ was joined to a human $IgG_4$ constant region within the pSV2-gpt expression vector (23, 4). The coding sequences of the MPC11 and cDNA genes are shown as solid and hatched lines, respectively. The dotted boxes represent the coding sequences of the human $IgG_4$ constant region. The maps are not drawn to scale.

Cloning and Expression of Chimeric Heavy Chains With Variable Regions Derived From Anti-dextran Hybridomas. The expressed $V_H$ regions from the three hybridoma antibodies to alpha (1→6) dextran were joined to the human $IgG_4$ constant region gene (FIG. 1) and after transfection of D3, a cell line producing only the hybridoma specific light chain (4,5), directed the expression of an H chain which assembled with the endogenous light chain and was secreted (results not shown). The nucleotide sequence of the variable regions of the heavy chain ($V_H$) and of the light chain ($V_L$) were determined (2) (Table I).

TABLE I

Immunochemical properties of Hybridoma Antibodies Specific for Dextran B512

| Hybridoma | Mouse Strain Origin | Isotype | Site Size[c] | Ka (ml/g)[d] Dextran | $K_ia$ $(M^{-1})^{d,e}$ (IM7) | Heavy Chains amino acid changes v. 14.6b.1 prototype[f] | | | |
|---|---|---|---|---|---|---|---|---|---|
| | | | | | | CDR1 | CDR2 | CDR3 | $J_H$ |
| 14.6b.1[a] | BALB/c | IgA, k | 6 | $4.43 \times 10^5$ | $5.76 \times 10^4$ | — | — | −3 | |
| 5.54.4.24.1[b] | C57BL/6 | IgA, k | 6 | $1.78 \times 10^4$ | $3.02 \times 10^3$ | 31 Ser→Gly | 60 Thr→Asn | −3 | |
| 19.22.1[a] | BALB/c | IgM, k | 7 | $8.87 \times 10^3$ | $6.46 \times 10^3$ | — | 60 Thr→Asn | −3 | |

[a]According to Sharon et al. (1).
[b]According to Newman et al. (20).
[c]Maximum number of alpha (1→6) linked glucose residues that fit the antibody combining site.
[d]Determined by affinity gel electrophoresis according to the method described by Takeo and Kabat (21).
[e]Association constant of anti-dextran combining sites with isomaltoheptaose (IM7).
[f]According to Alkolkar et al. (2).

Figure 2A:
FIGS. 2A and 2B. SDS-polyacrylamide gel electrophoresis (SDS-PAGE) analysis of immunoprecipitates obtained after papain digestion of FIG. 2A) [$^{35}$S]-Met or FIG. 2B) [$^{14}$C]-glucosamine labelled secreted Ig. Secretions of cells labelled in the presence of 15 micro Ci/ml of [$^{35}$S]-Met or 100 micro Ci/ml [$^{14}$C]-D-glucosamine hydrochloride (24) were digested with papain (Sigma Chemical Co., St. Louis, Mo.) at 1:100 enzyme:protein ratio for four hours at 37° C. The reaction was stopped by addition of iodoacetamide to 0.03 M. The Fc fraction and undigested antibody protein were precipitated by incubation with IgG Sorb (Enzyme Center, Malden, Mass.). Antigen binding fragment (Fab) was precipitated from the supernatant using rabbit anti-human Fab or by insolubilized dextran (Sephadex® G75). Samples were reduced with beta-mercaptoethanol. (0.15 M) and analyzed using 5% SDS-PAGE (16). The heavy chains produced by the transfectant cell lines are as follows: THV8, $V_H$ 19.22.1; TJC8.5, $V_H$ 5.54.4.24.1; TKC3.2, $V_H$ 14.6b.1; all transfectants synthesize the alpha (1→6) dextran specific light chain. [$^{35}$S]-Met labelled and reduced Igs were used as markers.

To determine if the 14.6b.1 chimeric antibody contained carbohydrate in $V_H$ the molecule was fractionated into Fab and Fc by papain cleavage, then the molecules were reduced with beta-mercaptoethanol, and analyzed on 5% SDS-PAGE gels. Proteins were labelled with [$^{35}$S]-Met and the Fab precipitated using specific anti-Fab anti-serum (FIG. 2A). Transfectoma antibodies with $V_H$ derived from 5.54.4.24.1 and 19.22.1 cDNA clones (TJC8 and THV8, respectively) show comigration of their Fd and kappa light chains. In contrast in transfectoma antibodies whose H chain variable region is from 14.6b.1 (TKC3.2) the Fd portion migrates more slowly than the L chain. The reduced mobility of the 14.6b.1 Fd fragment is consistent with glycosylation of its $V_H$.

Figure 2B:
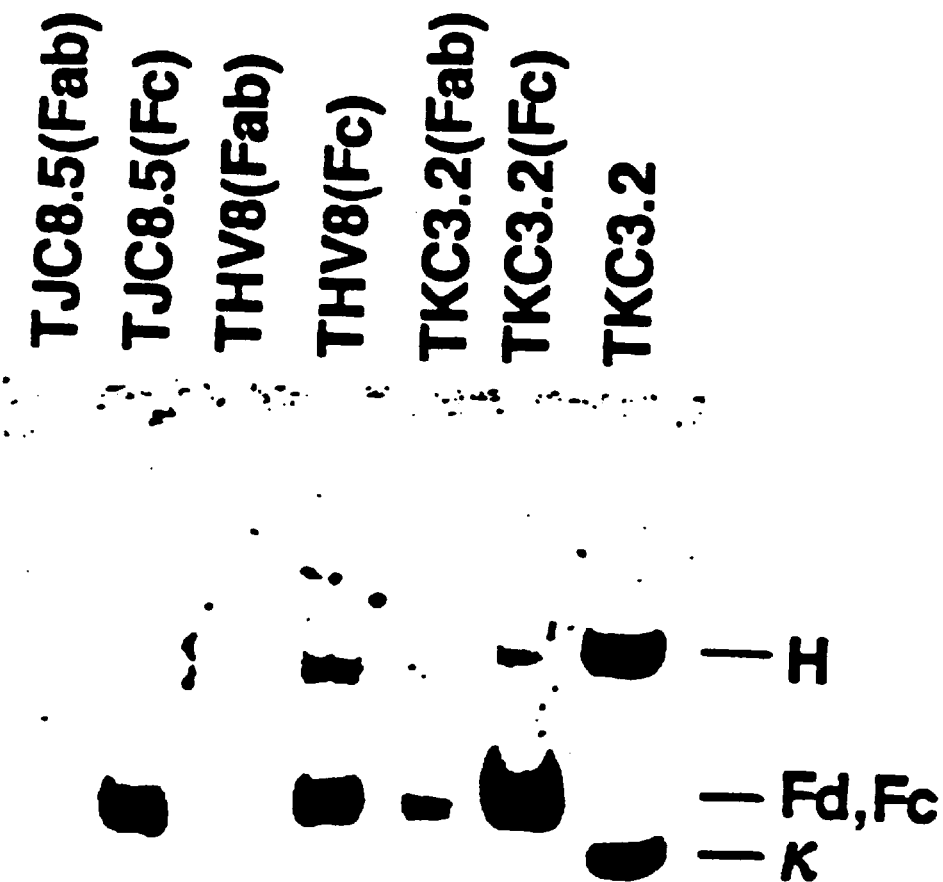

To confirm the presence of carbohydrate in the $V_H$ of 14.6b.1, the secreted immunoglobulin was labelled with [$^{14}$C]-glucosamine, Fab and Fc fractions were prepared and the products analyzed by SDS-PAGE (FIG. 2B). As anticipated the kappa light chains do not contain carbohydrate and bands are absent. [$^{14}$C]-glucosamine labelling of the human IgG Fc fragment was found which contains N-linked carbohydrate within its $C_H2$ domain (6). However, only TKC3.2(Fab) with its Fd obtained from the 14.6b.1 $V_H$ shows glucosamine labelling. The reduced intensities of the Fd bands relative to the Fc is probably due to poor recovery of the Fab fragment rather than incomplete glycosylation (7). In SDS-PAGE gels in which H chains could be resolved containing no, one or two carbohydrate moieties (FIG. 3A), only one heavy chain band for TKC3.2 was found.

Role of the Carbohydrate in the Antigen-Antibody Interaction. To examine the role of carbohydrate in antigen binding, the association constants for tunicamycin treated aglycosylated and untreated native anti-dextran transfectoma antibodies were determined. Although tunicamycin is a potent inhibitor of N-linked glycosylation (8), it is difficult to produce proteins completely free of glycosylated species. From reconstruction experiments it was apparent that even a trace contamination of high affinity antibody could dramatically increase the apparent binding constant for dextran of the low affinity antibody (data not shown). To avoid this Con A was used which binds high mannose and biantennary complex oligosaccharides (9) to separate unglycosylated from glycosylated immunoglobulin. Adsorption experiments showed that the carbohydrate in THV8.3 antibody ($V_H$ 14.6b.1) was not absorbed to Con A sepharose (FIG. 3A, lanes 2 and 4). The residual TKC3.2 antibody seen in the Con A supernatant (lane 2) may reflect the inability to separate the Con A slurry completely from the culture fluid.

Figure 3B:
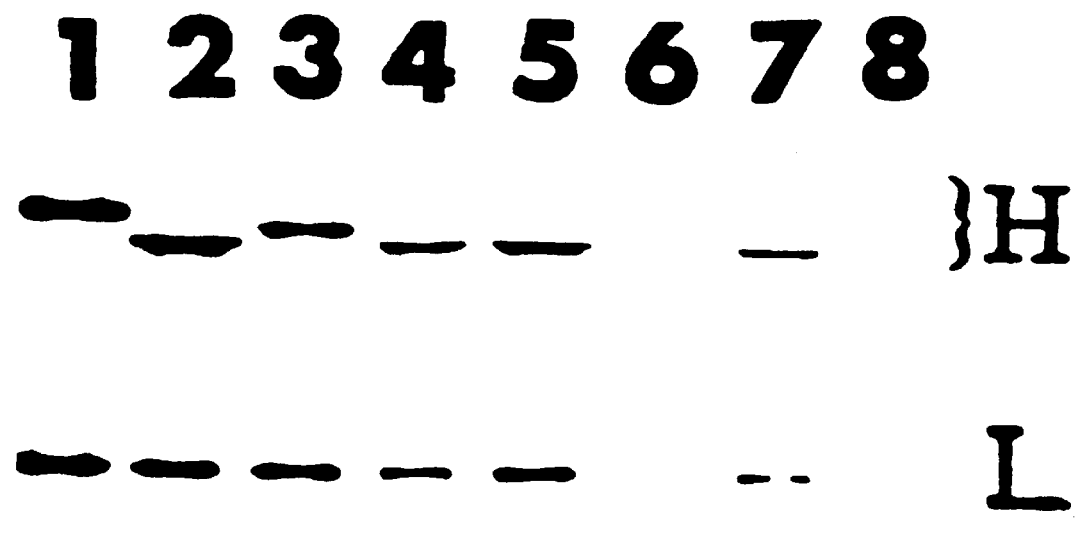

Tunicamycin treatment of both TKC3.2 and THV8.3 antibodies resulted in an electrophoretic mobility change consistent with the loss of carbohydrate from the H chain (FIG. 3B, lanes 1–4). H chains which contain two, one and zero-N linked carbohydrate moieties (lanes 1, 3 and 2 or 4, respectively) can be resolved. The H chain bands of the untreated samples (lanes 1 and 3) appear homogeneous suggesting all H chains are uniformly glycosylated. From the lack of visible glycosylated H chain bands in lanes 2, 4 and 6 it was estimated that tunicamycin treatment results in greater than 97% deglycosylation of the immunoglobulin. Lanes 5–8 show the results obtained from Con A adsorption of tunicamycin treated immunoglobulin. Both the TKC3.2 ($V_H$ 14.6b.1) and THV8.3 ($V_H$ 19.22.1) aglycosylated antibodies were not bound by Con A (lanes 5 and 7).

Having established that Con A adsorption could remove glycosylated contaminants from TKC3.2 tunicamycin treated preparations, Con A absorbed material was next used for dextran binding studies. The results from one typical experiment are graphically illustrated in FIG. 4. For the native TKC3.2 antibody ($V_H$ 14.6b.1) 50% inhibition of binding to ELISA plates coated with 0.5 micrograms/ml or 20 micrograms/ml dextran was obtained when 1.2 micrograms/ml of dextran inhibitor was added. Carbohydrate depleted TKC3.2 antibody ($V_H$ 14.6b.1) could not bind to 0.5 micrograms/ml dextran coated plates (data not shown). Using low affinity binding conditions (microtiter wells coated with 20 micrograms/ml dextran) the aglycosylated TKC3.2 ($V_H$ 14.6b.1) antibodies, and native THV8.3 antibody showed 50% maximal binding when 18–24 micrograms/ml dextran B512 inhibitor was added.

The apparent association constants for tunicamycin treated aglycosylated and untreated native anti-dextran antibodies are summarized in Table II.

TABLE II

Apparent Binding Constants for Dextran B512.

| Hybridoma or Transfectoma Ab | aKa (ml/g) Tabulated from[a] FIG. 4) | aKa (ml/g) Calculated from Several Experiments |
|---|---|---|
| 14.6b.1 | n.d[b] | 2.30 ± 0.1 × 10⁶ (4)[c] |
|  |  | (4.43 × 10⁵)[३] |
| 19.22.1 | n.d | n.d. |
|  |  | (8.87 × 10³)[d] |
| TKC3.2 (−Tm) | 1.7 × 10⁶ | 1.68 ± 0.6 × 10⁶ (8)[e] |
|  |  | (2.10) ± 0.3 × 10⁶)[g] (5) |
| TKC3.2 (+Tm) Con A adsorbed | 1.1 × 10⁵ | 1.18 ± 0.04 × 10⁵ (5) |
| THV8.3 (−Tm) | 1.0 × 10⁵ | 8.22 ± 3.6 × 10⁴ (10)[f] |
|  |  | (6.5 ± 0.3 × 10⁴)g (6) |
| THV8.3 (+Tm) Con A adsorbed | 8.3 × 10⁴ | 1.09 ± 0.4 × 10⁵ (4) |

[a]Calculated from the reciprocal concentration of dextran B512 necessary to inhibit 50% of the maximal binding of antibody to dextran coated plates. The $1/[Dex]_{I50}$ concentration has been multiplied by a factor of 2 to give the final aKa value because dextran inhibitor and antibody were added to microtiter wells at a 1:1 molar ratio.
[b]Not determined.
[c]The aka value represents an average obtained from the number of experiments indicated in parenthesis. The error for the sum of all the values is represented by the first standard deviation.
[d]Determined using the affinity gel electrophoresis method.
[e,f]antibody concentrations were 0.8 micrograms/ml and 0.3 micrograms/ml, respectively.
[g]Culture supernatants were not from tunicamycin experiments. Antibody concentration was 1 microgram/ml.

To determine antibody concentrations culture supernatants diluted into BBS (0.02M borate-buffered, 0.75% saline, pH 8.3) were bound to polystyrene microtiter wells (Corning, N.Y.) for three hours at 37° C. After blocking any unreacted sites with 1% bovine serum albumin/0.05% Tween® 20 PBS (PBS•T•S) for one hour at room temperature, the Enzyme-linked immunosorbent assay (ELISA) plates were washed with PBS/0.5% Tween three times, PBS once, and then bound Ig was quantitated by reaction with horse-radish peroxidase labelled anti-human IgG antibody and comparison to a human IgG standard of known concentration. Assay results have been reproduced at least three times.

The binding constant of the carbohydrate depleted TKC3.2 antibody ($V_H$ 14.6b.1) was 14–15 fold lower than the native antibody. In contrast, carbohydrate removed from the Fc of THV8.3 ($V_H$ 19.22.1) did not affect the ability of the antibodies to bind antigen. All experiments except those noted were performed using an antibody concentration of 1 microgram/ml. A slight effect of antibody concentration on apparent aKa values was observed. The aKa values determined using the inhibition ELISA were, in general 3–5 fold higher than those obtained by affinity gel electorphoresis but the differences in binding strength between antibodies were similar using the two assays. A 32-fold difference in binding affinity between the TKC3.2 ($V_H$ 14.6b.1) and THV8.3 ($V_H$ 19.22.1) antibodies was found, versus the 50-fold difference between 14.6b.1 and 19.22.1 reported previously (10). In summary it is clear that the presence of carbohydrate within the anti-dextran $V_H$ region significantly affects its affinity for antigen, however, an additional contribution of the altered amino acids to the differences in binding cannot be ruled out.

Structure of the Carbohydrate Moieties on the Heavy Chain. Finally, glycohydrolase Endo H was used to investigate the structure of the $V_H$ oligosaccharide. The di-N-acetylchitobiose linkage of high mannose core oligosaccharides found on newly synthesized IgG H chains is susceptible to Endo H cleavage (11), while processed complex carbohydrates are resistant to Endo H cleavage. H chains obtained from cell cytoplasms were hydrolyzed by Endo H (data not shown). In contrast, heavy chains from the secretions of both THV8.3 and TKC3.2 were unaltered by Endo H treatment.

Potential Significance of Carbohydrate in Antibody Function. Antibodies are glycoproteins with all heavy chains containing at least one and frequently several N-linked carbyhydrate residues (12). The role postulated for carbohydrate found on the heavy chain constant regions includes solubilization of the H chain, facilitation of subcellular transport and secretion, promotion of assembly, and maintenance of immunoglobulin conformational features which contribute to effector functions (13). Carbohydrate can also be found within the V region of an antibody molecule. Fifteen percent of human myeloma light chains have carbohydrate within their variable regions. (14). In a study of 76 human IgG myeloma proteins, approximately 25% were shown to contain a carbohydrate moiety on the Fab fragment (15). The carbohydrate was linked to either the light chains or the Fd fragments, and in a few cases to both.

Experimental Discussion

In the present invention it has been directly demonstrated that the presence of carbohydrate in CDR2 of $V_H$ is critical for the high affinity binding of a monoclonal antibody specific for polymeric alpha (1→6)-dextran and from this it can be inferred that the carbohydrate also contributes to the increased affinity for IM7. Thus not only the specific amino acid sequence of the variable region, but also its carbohydrate moieties can determine the specificity and magnitude of the antigen-antibody interaction.

In an earlier study Matsuuchi et al. (16) isolated and characterized a spontaneously arising mutant of the myeloma J558 (IgA, lambda, anti-alpha (1→3) dextran) with decreased reactivity with polymeric dextran. The mutant differed from the wild-type in that it had increased amounts of sialic acid on the carbohydrate in its Fab region. Because the variable region of J558 does not contain the canonical carbohydrate addition sequence, the altered carbohydrate probably resides within the $CH_1$ domain. The change in carbohydrate content was the consequence of the altered availability of cellular enzymes involved in glycosylation.

Labeta et al. have reported that the affinity of an anti-DNP antibody for hapten DNP-GABA-BSA was significantly increased after Endo H cleavage of the Fab carbohydrate (17). In contrast and in accordance with the present invention the absence of carbohydrate from the fragment antigen binding (Fab) of an antibody to alpha (1→6)-dextran decreased the affinity of the antibody for antigen.

Of great interest is the mechanism by which presence of an oligosaccharide attached to amino acids in the combining site of the antibody 14.6b.1 leads to increased Ka for both polymeric dextran and IM7. Both comparison with X-ray crystallographic studies of unrelated antibodies which predict that residues to which the carbohydrate is attached in $V_H$ should be exposed on the hypervariable loops and the Con A adsorption experiments of this invention, suggest that the $V_H$ oligosaccharide is relatively exposed and positioned at the surface of the Ig. Although sugar-sugar contacts between the two oligosaccharides in $CH_2$ of the constant region have been documented (18), it is difficult to see how direct interactions could occur both with polymeric dextran and a site filling oligosaccharide, IM7.

A more likely explanation for the effect of glycosylation is that the carbohydrate linked to amino acid 58 alters the conformation of the combining site. Such alterations might increase the accessibility of the threonine residue at position 60 in the 14.6b.1 $V_H$ region so that it may contact the antibody more closely. Indeed, Feldman and coworkers have predicted from the hypothetical space-filling model of the V-region of the galactan-binding myeloma Ig J539 that H chain Thr residue 56 may contact galactan (19). The X-ray crystallographic structure of the 14.6b.1 Fab would aid in the understanding of how the presence of carbohydrate affects the topology of the combining site.

Second Series of Experiments

Production of Antibodies With Altered Carbohydrate in Constant Region. All four human IgG subclasses contain a consensus glycosylation sequence Asn-X-Thr/Ser (X—any amino acid) in the $C_H2$ domain. Several reports have indicated that this carbohydrate side chain is important for the effector functions of immunoglobulins, including Fc receptor binding and complement activation (22, 23). Site-directed mutagenesis was used to remove this carbohydrate addition signal from the $C_H2$ domain so molecules deficient in carbohydrate, could be produced for use in assessing the role of carbohydrate in biological functions. Until now, researchers have used for this purpose immunoglobulins produced by cells grown in the presence of tunicamycin, an inhibitor of N-linked glycosylation. However, using that approach, only small quantities of protein could be produced, and it was difficult to assure that the resulting proteins were totally deficient in carbohydrate.

Many different approaches exist for site-directed mutagenesis; one approach used in the present invention is illustrated in FIG. 5 (24). The Sal I-Bam HI fragment containing the IgG constant region exon is cloned into the M13 phage M13mp19 at the polylinker site. The positive-strand DNA template of the recombinant phage is prepared by the standard polyethylene glycol method. Two primers are used to produce the mutation, one the M13 sequencing primer, the other a 5' end-phosphorylated mutagenic primer with one nucleotide mismatched in the consensus glycosylation sequence. Both primers are annealed to the template at the same time. After primer extension and ligation, the mutant/wild-type-gapped heteroduplex is used to transform E. coli host JM109. To distinguish mutants from wild type phage clones, colony hybridization is employed. Under low stringency hybridization conditions, both the mutant and the wild type phage hybridize with the mutagenic oligomer. When the stringency of the hybridization conditions is increased, e.g., by increasing the temperature at which the hybridized phage plaques are washed, the labeled mutagenic oligomer remains hybridized with the mutant phage DNA but dissociates from the nonmutant phage DNA. Finally, the exact nucleotide change introduced into the immunoglobulin heavy chain must be confirmed by sequencing the DNA; the dideoxy method of sequencing is used (25, 26). The mutagenized gene is then transferred into an expression vector, where it can be used to direct the synthesis of an altered protein. This general approach can be used to introduce changes anywhere within the antibody molecule and may have particular application to the production of antibody molecules with altered idiotypes.

Using the method described in this section, antibodies deficient in constant region carbohydrate have been produced. These exhibit altered effector functions: decreased ability to bind Fc receptors and activate complement. One ($\gamma_3$) shows a decreased serum half-life in mice while the half life of the second ($\gamma_1$) appears unchanged.

This approach could also be used to put additional carbohydrate molecules in the constant region. This could be useful when ligands are attached to antibodies via their carbohydrate.

References

1. J. Sharon, E. A. Kabat, and S. L. Morrison, *Molec. Immunol.,* 19, 389, (1982).

2. P. N. Alkolkar, S. K. Sikder, S. B. Bhattacharya, J. Liao, F. Gruezo, S. L. Morrison and E. A. Kabat, *J. Immunol.* 138, 4472, (1987).
3. G. M. Griffiths, C. Berek, M. Kaartinen, and C. Milstein, *Nature (London)* 312, 271, (1984).
4. V. T. Oi, S. L. Morrison, L. A. Herzenberg and P. Berg, *Proc. Natl. Acad. Sci. U.S.A.* 80, 825 (1983).
5. L. K. Tan, V. T. Oi, and S. L. Morrison, *J. Immunol.* 135, 3564, (1985).
6. E. W. Silverton, M. A. Navia, and D. R. Davis, *Proc. Natl. Acad. Sci. U.S.A.* 74, 5140, (1977).
7. D. R. Anderson, P. Samaraweera, and W. J. Grimes, *Biochem. Biophys. Res. Commun.* 116, 771, (1983).
8. A. D. Elbein, *Trends in Biochemical Sciences* 6, 219 (1981).
9. D. R. Anderson and W. J. Grimes, *J. Biol. Chem.* 257, 14858 (1982).
10. J. Sharon, E. A. Kabat and S. L., Morrison, *Molec. Immunol.* 18, 831, (1981).
11. P. W. Robbins, S. C. Hubbard, S. J. Turco and D. F. Wirth, *Cell* 12, 893 (1977).
12. C. Sidman, *J. Biol. Chem.* 256, 9374 (1981).
13. A. Shimizu, F. W. Putnam, C. Paul, J. R. Clamp. and I. Johnson, *Nature New Biology* 231, 73 (1971).
14. H. S. Sox, Jr. and L. Hood, *Proc. Natl. Acad. Sci. U.S.A.* 66, 975, (1970).
15. H. L. Spiegelberg, C. A. Abel, B. G. Fishkin, and H. M. Grey, *Biochemistry* 9, 4217 (1970).
16. L. Matsuuchi, L. A. Wims and S. L. Morrison, *Biochemistry* 20, 4827, (1981).
17. M. O. Labeta, R. A. Margni, J. Leoni, and R. A. Binaghi, *Immunology* 57, 311 (1986).
18. B. J. Sutton and D. C. Phillips, *Biochem. Soc. Trans.* 11, 130 (1983).
19. R. J. Feldmann, M. Potter, and C. P. J. Glaudemans, *Molec. Immunol.* 18, 683 (1981).
20. B. A. Newman and E. A. Kabat, *J. Immunol.* 135, 1220 (1985).
21. K. Takeo and E. A. Kabat, *J. Immunol.* 121, 2305, 1978.
22. S. L. Morrison, L. A. Wims, S. C. Wallick, L. K. Tan and V. T. Oi, *Annals N. Y. Acad. Sci.* (in press).
23. J. Dangyl, T. Wensel, L. Stryer, S. L. Morrison, L. A. Herzenberg, and V. T. Oi, in press.
24. S. L. Morrison, *J. Immunol.* 123, 793 (1979).
25. A. Nieto, A. Gaya, M. Jansa, and J. Vives, *Molec. Immunol.* 21, 537 (1984).

What is claimed is:

1. A method of altering affinity of an antibody for an antigen to which it is directed, wherein the method comprises:

(a) measuring the affinity of an unaltered antibody for the antigen, (b) deleting DNA encoding a carbohydrate recognition site from DNA encoding the variable region of the antibody thereby producing a mutagenized gene encoding an altered antibody;

(c) expressing the mutagenized gene encoding the altered antibody to produce an altered antibody;

(d) measuring the affinity of the altered antibody for the antigen; and (e) determining that the affinity measured in step (a) is different from the affinity measured in step (d), wherein the carbohydrate recognition site comprises Asn-X-Thr/Ser, wherein X indicates any amino acid and wherein Thr/Ser indicates either threonine or serine.

2. The method of claim 1, wherein the antibody is a monoclonal antibody.

3. The method of claim 2, wherein the antibody is a human antibody.

4. The method of claim 2, wherein the antibody comprises a constant region from an antibody of one species and comprises a variable region from an antibody of another species.

5. The method of claim 2, wherein the antibody is a humanized antibody.

6. The method of claim 1, wherein the carbohydrate recognition site is deleted from the variable region of the antibody by site-directed mutagenesis of DNA encoding the variable region of the antibody.

7. A method of altering affinity of an antibody for an antigen to which it is directed, wherein the method comprises:

(a) measuring the affinity of an unaltered antibody for the antigen, (b) introducing DNA encoding a carbohydrate recognition site into DNA encoding the variable region of the antibody, thereby producing a mutagenized gene encoding an altered antibody;

(c) expressing the mutagenized gene to produce an altered antibody under conditions such that a carbohydrate binds to the carbohydrate recognition site;

(d) measuring the affinity of the altered antibody for the antigen; and (e) determining that the affinity measured in step (a) is different from the affinity measured in step (d), wherein the carbohydrate recognition site comprises Asn-X-Thr/Ser, wherein X indicates any amino acid and wherein Thr/Ser indicates either threonine or serine.

8. The method of claim 7, wherein the antibody is a monoclonal antibody.

9. The method of claim 8, wherein the antibody is a human antibody.

10. The method of claim 8, wherein the antibody comprises a constant region from an antibody of one species and comprises a variable region from an antibody of another species.

11. The method of claim 8, wherein the antibody is a humanized antibody.

12. The method of claim 7, wherein the carbohydrate addition site is introduced into the variable region of the antibody by site-directed mutagenesis of DNA encoding the variable region of the antibody.

* * * * *